(12) United States Patent
Ashdown

(10) Patent No.: US 6,642,012 B1
(45) Date of Patent: Nov. 4, 2003

(54) SPECTROSCOPIC DETERMINATION OF CHARACTERISTIC OF BIOLOGICAL MATERIAL

(76) Inventor: Martin Leonard Ashdown, 140 Keon Street, Thornbury, Victoria, 3071 (AU)

( * ) Notice: Subject to any disclaimer, the term of this patent is extended or adjusted under 35 U.S.C. 154(b) by 0 days.

(21) Appl. No.: 09/125,837

(22) PCT Filed: Feb. 26, 1997

(86) PCT No.: PCT/AU97/00112

§ 371 (c)(1),
(2), (4) Date: Aug. 26, 1998

(87) PCT Pub. No.: WO97/32194

PCT Pub. Date: Sep. 4, 1997

(30) Foreign Application Priority Data

Feb. 26, 1996 (AU) .............................................. PN8257

(51) Int. Cl.⁷ ........................ G12Q 1/02; G01N 33/487
(52) U.S. Cl. ............................ 435/7.24; 435/2; 435/4; 435/7.21; 435/7.23; 435/29; 436/63; 436/64; 436/171; 436/805
(58) Field of Search ............................ 435/2, 4, 7.21, 435/7.24, 29, 7.23; 436/63, 64, 171, 805

(56) References Cited

U.S. PATENT DOCUMENTS

| | | |
|---|---|---|
| 5,146,091 A | 9/1992 | Knudson .................... 250/341 |
| 5,387,524 A | 2/1995 | Hayashibe et al. ........... 436/74 |
| 5,473,160 A | 12/1995 | Eysel et al. ............ 250/339.12 |

FOREIGN PATENT DOCUMENTS

| | | |
|---|---|---|
| EP | 0 637 472 A1 | 2/1995 |
| WO | 92/14134 | 8/1992 |
| WO | 93/16370 | 8/1993 |
| WO | 94/01749 | 1/1994 |
| WO | WO 96/00892 A1 | 1/1996 |
| WO | WO 96/41153 A1 | 12/1996 |

OTHER PUBLICATIONS

Le Gal et al, Cancer Research, 53, 3681–3686, 1993.*
Jackson et al, Biochemistry, 30, 9681–9686, 1991.*
Manfait et al, Biochemical and Biophysical Research Communications, 116, 321–326, 1983.*
Paul, Fundamental Immunology (Third Ed.), Raven Press, 1993, Chapter 13, pp. 467–504, 1993.*
Trewhella et al, Biochemistry, 28, 1294–1301, 1989.*
Huschtscha et al, International Journal of Oncology, 6, 585–593, 1995.*

* cited by examiner

Primary Examiner—David Saunders
(74) Attorney, Agent, or Firm—Nixon & Vanderhye P.C.

(57) ABSTRACT

Method for determining a cellular function or change in cellular function by contacting a sample of cells or a component of cells with an activating agent, directing a beam of infrared light at the sample of cells or a component of the cells, analyzing the infrared spectrum of the sample at at least one range of frequencies and ascertaining whether at least one change in the spectral characteristics has occurred due to activation of the cells or a change in the cellular component, that can be correlated to the cellular function or the change in cellular function by the activating agent and determining the cellular function therefrom.

19 Claims, 1 Drawing Sheet

SPECTROSCOPIC DETERMINATION OF CHARACTERISTIC OF BIOLOGICAL MATERIAL

The present invention relates to a spectroscopic method for the investigation of biological material. The invention is particularly concerned with the application of Infrared (IR) spectroscopy (spectrometry) in the investigation of blood or other body fluids or one or more components thereof.

An example of an investigation in accordance with the invention is the determination of cellular immunity in patients with immunodeficiency, autoimmunity, contact with infectious diseases, allergies, hypersensitivities, and cancer. The investigation may be related to determining tissue compatibility for transplants.

BACKGROUND OF THE INVENTION

Currently there are a number of clinical laboratory methods of determining cellular immunity. The delayed hypersensitivity skin test is one tool that occasionally serves to establish a diagnosis in areas such as allergy studies. However patients who are highly sensitive to various antigens will have marked reactions to such skin tests. In some cases skin tests cannot be performed at all to avoid challenging the patient with potentially hazardous antigens.

Another technique for determining cellular immunity is lymphocyte activation. Lymphocyte activation, also known as lymphocyte stimulation, refers to an in vitro correlate of an in vivo process that generally occurs when antigen reacts or interacts with specifically sensitized lymphocytes in the host. The lymphocyte activation or stimulation test is one in which lymphocytes are extracted from whole blood and incubated with an antigen. Tritiated thymidine is then added over a 16 hour period before the cells are harvested and their radioactivity measured by use of a liquid scintillation counter. This in vitro technique may be used to assess cellular immunity in patients with immunodeficiency, autoimmunity, infectious diseases, allergies or hypersensitivities and cancer and in the area of transplantation compatibility.

The disadvantages of existing in vitro assays based on lymphocytes and monocytes is that they are time consuming, labour intensive, imprecise and expensive because of the reagents, equipment and highly qualified labour required.

SUMMARY OF THE INVENTION

I have found surprisingly that IR spectroscopy may be used to investigate blood or other body fluid or component(s) thereof. The use of IR spectroscopy has the advantages of providing results relatively quickly with less labour input when compared to the conventional methodology. Moreover the use of IR spectroscopy may provide a more precise indication of a characteristic of a blood or body fluid component. A further advantage of the use of IR spectroscopy is that it allows the identification of dynamic processes through changes in the IR spectra.

The term body fluid components include sweat, saliva, urine, semen and lacrimal secretions.

IR spectroscopy is routinely used by organic chemists and biochemists and others as a molecular probe. When infrared light is passed through a sample of an organic compound, some of the frequencies are absorbed while other frequencies are transmitted through the sample without being absorbed. By IR spectroscopy we also include Laser-Raman spectroscopy including Raman confocal laser spectroscopy or any other IR spectroscopy technique.

Organic applications of IR spectroscopy are almost entirely concerned with frequencies in the range 650–4000 $cm^{-1}$. Frequencies lower than 650 $cm^{-1}$ are called far infrared and those greater than 4000 $cm^{-1}$ are called near infrared.

Conventional IR spectrometers suffer disadvantages in sensitivity, speed and wavelength accuracy. Most spectrometers scan over the wavelength range and disperse infrared light using a grating or prism. These dispersive infrared spectrometers suffer from wavelength inaccuracies associated with backlash in the mechanical movement, such as rotation of mirrors and gratings.

An entirely different principle is involved in Fourier Transform infrared (FTIR) spectroscopy, which centres on a Michelson interferometer. The FTIR spectrometer has the advantage of speed and sensitivity in which picogram quantities of sample can give good spectra.

The present invention provides, in one aspect, a method for the investigation of:
  at least one component of blood or other body fluid;
  the change(s) in the at least one component;
  the functional status of the at least one component; or
  the change in the functional status of the at least one functional component
the method including directing infrared light through a sample containing the at least one component and analysing the absorption characteristics of said sample.

Preferably the method of the invention is carried out using FTIR spectroscopy but other IR spectroscopic techniques may be used.

The absorption characteristic determined may be those in the region of symmetric and antisymmetric stretching modes of phosphodiester groups, the C—O stretching mode, the $CH_2$ bending mode, and the amide I and II bands. The absorption characteristics analysed may be those due to functional group vibration in signature molecules or groups, for example, the phosphodiester group of nucleic acids, COH groups, C—O groups of, for example, fatty acyl groups or glycogen bands, carbohydrates or due to lipid molecules present in the specimen.

The reference to blood and body fluid components may include, but is not limited to, single or mixed cell populations, a single simple biochemical component or complex mixtures of biochemical components derived or prepared from blood or body fluids.

The investigation may be carried out on whole blood or other body fluid or an extract of component thereof. The component may be, for example, lymphocytes, erythrocytes or platelets.

The method of the present invention has particular application in the determination of cellular function or change in cellular function.

Accordingly, in a further aspect, the present invention provides a method for determining a cellular function or change in cellular function of cells, the method including:
  contacting a sample of the cells or a component of the cells with an activating agent;
  directing a beam of infrared light at the sample of a cells;
  analysing the infrared absorption of the sample at at least one range of frequencies; and
  ascertaining whether at least one charge in the absorption characteristic has occurred due to activation of the cells by the activation agent and determining the cellular function or change in cellular function therefrom or correlating the change in component of the cell to a change in the cellular function.

The cellular function determined may be any function that is an indicator of viability, integrity or functional status of the cells. The functional status may be immune competence.

The cells used in the method of the invention may be selected from lymphocytes or erythrocytes. Preferably the cells are lymphocytes.

Lymphocytes may be isolated by purification of anticoagulated peripheral blood by any suitable technique, for example density gradient centrifugation or use of magnetic beads.

The activating agent may be a biological or non-biological agent(s). These agents may be naturally derived or synthetic. Examples of these biological or non-biological agents include, but not limited to:

a) Mitogens which are non-specific agents which stimulate or activate large numbers of lymphocytes and do not require a sensitized host. Mitogens cause a myriad of biochemical events and ultimately division of lymphocytes. Examples of mitogens include concanavilin A, phytohaemagglutinin, Staphylococcus Protein A, pokeweed mitogen, phorbol mystirate acetate and Streptolysin S.

b) Potential antigens or previously encountered antigens which have a sensitized host and stimulate specific cells, in most instances, T or B lymphocytes or other immunocompetent cells that are or become specifically sensitized to the antigens in question. Antigens may include but not be limited to:

i) live, attenuated or dead microorganisms or components or products from microorganisms whether naturally occurring, synthetic or genetically engineered such as cell surface lipopolysaccharide or toxins, for example, Candida antigen, Streptokinase, tetanus toxoid, vaccinia virus, and Herpes simplex virus;

ii) cells or cellular components or products derived from plants, animals, whether naturally occurring, synthetically induced, genetically engineered including cell surface components. Included in this category are antigens, either presented on cells or isolated from cells such as Histocompatibility antigens, ABO blood group antigens, virally induced cell components or surface markers, cell developmental or differentiation markers, tumour-induced or tumour-specific components, and haptens or moieties whose binding to cell subsequently induces the cells to become stimulated or activated or whose binding to isolated cell components causes an alteration which can be correlated to cell stimulation or activation.

c) Monoclonal or polyclonal antibodies to lymphocyte cell surface molecules which can result in activation or cell death.

I have found that the dynamic cellular processes which are known to occur in lymphocyte activation/stimulation are manifest as changes over time in the infrared spectral profile of the activated lymphocytes compared to unactivated lymphocytes. The determination of the invention may be carried out by measuring the IR spectral profile of the sample and comparing that with the "normal" or alternatively by investigating the change of the spectral profile over time.

The IR spectral profile may be determined two or more times over a period and the spectral profiles compared to determine whether at least one change in an absorption characteristic in one or more regions of the profiles has taken place. I have found that in some instances changes in the spectral profile may take place within 30 minutes.

Alternatively, the determination may be carried out by taking an infrared spectrum of a sample and comparing it with a standard spectrum and ascertaining whether there is at least one differences in an absorption characteristic in one or more regions of the profiles.

In yet another aspect the present invention provides a method for the determination of the immunocompetence and/or disease status of a human or animal subject, the method including taking a sample of blood or other body fluid from the subject and subjecting the sample or an extract therefrom, optionally after being contacted with a stimulating agent, to infrared radiation to provide an IR spectral profile thereof and determining the lymphocyte function and/or activation as a measure of the immunocompetence and/or disease status of the subject.

The present invention may also be used to investigate the viability and functional integrity of blood or a blood component such as erythrocytes or platelets over time and conditions of storage. This can be achieved by comparing the IR spectra profile with the profile of "fresh" material and determining whether there are any differences in the spectra. This has particular application in blood banks and the like where the present invention provides a relatively speedy method of determining the viability and functional integrity of stored blood.

EXAMPLES

Figure 1:
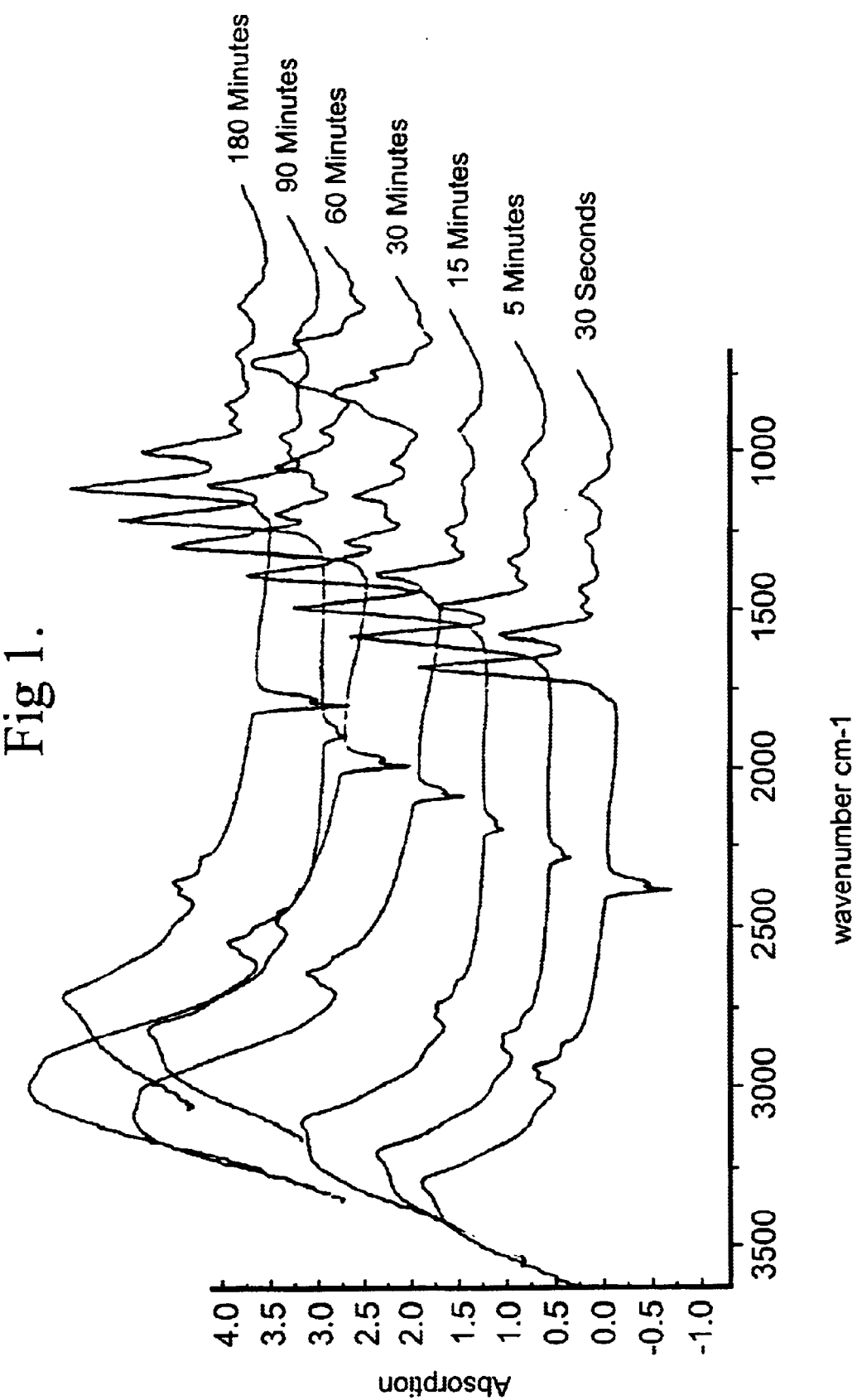
FIG. 1 is a series of spectral profiles taken at intervals from 30 seconds through to 180 minutes.

In order to assist in an understanding of the present invention we provide the following non-limiting examples.

Example 1

FTIR Monitoring of Lymphocyte Activation

Peripheral blood mononuclear cells (PBMC) from two volunteers, isolated using gradient mixtures were twice washed in 0.9% saline and centrifuged. The resulting pellets were resuspended in 1 ml of saline. One half of each sample was activated with phorbol myristate acetate (PMA) and the other half used as a control. After 15 minutes the four portions were desiccated and transferred to a infrared cell for FTIR microanalysis. For each portion six spectra were recorded.

A high quality, highly reproducible spectra of activated and non-activated lymphocytes from both volunteers resulted. Spectra of the activated lymphocytes exhibit marked differences to those of the non-activated lymphocytes. Spectra of activated lymphocytes are characterised by a reduction in the α-helical amide I band and an increase in the band associated with amide Iβ-pleated sheet component at 1634 cm.$^{-1}$. The amide II band exhibits a multitude of shoulder peaks indicative of β-turns associated with protein conformational changes. The C—O stretch of fatty acyl groups (1400 cm$^{-1}$) and the C—O stretches of glycogen bands at 1058 cm$^{-1}$ and 1038 cm$^{-1}$ are much more intense in activated lymphocytes. The band at 1295 cm$^{-1}$ appears to be shifted from 1286 cm.$^{-1}$ in the non-activated activated cells.

The results of these PMA experiments demonstrate the potential of FTIR spectroscopy to not only detect the initial allogeneic activation of lymphocytes but also provide a wealth of molecular information connected with the triggering of the immune response.

Example 2

Blood from two HLA disparate volunteers (L and P) was diluted in 0.9% saline. 10 ml of Lymphoprep™ was then carefully layered beneath the diluted blood and the tubes centrifuged at 2300 g for 15 min. The resulting lymphocyte layers were separately transferred, twice washed and centrifuged and finally resuspended in 2 ml of isotonic saline. Aliquots were collected from each tube and mixed in nine Eppendorf tubes and a further nine from P and nine from L were placed in separate Eppendorf tubes to serve as controls.

The lymphocytes were centrifuged at 2600 g for 5 minutes and placed in a 37° incubator. At times between 0 and 180 min., 100 μL volumes from the mixed, L and P tubes were transferred into the wells of a infrared cell and then rapidly desiccated. The resultant thin pellets were analysed with the FTIR microscope. Blood from the two HLA identical twins was used to obtain IR spectra following exactly the same methodology. Blood from 2 individuals with a 50% HLA disparity was worked up in the same manner but with tissue culture growth medium substituted for the isotonic saline as the incubation medium.

After 5 minutes (see FIG. 1) no apparent changes in the spectral profiles were evident. At 15 minutes there appears to be an increase in phosphate bands at 1238 cm$^{-1}$ and 1086 cm$^{-1}$ and after 30 minutes radical spectral changes are observed. The amide II band is reduced and shoulder peaks indicative of P turns associated with protein conformational changes have become more pronounced. The band at 1393 cm$^{-1}$ from the C—O stretch of fatty acyl groups has dramatically increased and a sharp band at 1286 cm$^{-1}$ has appeared. The PMA activated lymphocytes produced spectra with a similar band at 1295 cm$^{-1}$. The most striking features are observed in the carbohydrate/phosphodiester region (1200–1000 cm$^{-1}$), with a dramatic increase in bands associated with the C—O stretches of carbohydrates at 1004 cm$^{-1}$ and 1058 cm$^{-1}$. This feature was also observed in the spectra of lymphocytes activated with PMA and may reflect an increase in surface glycoproteins. After 60 minutes the spectral profile still resembles the 30 minute profile, however in the later samples these changes have dramatically resided indicating a quiescent period.

For the 50% HLA disparate individuals spectral changes almost identical to those above occurred but after a much longer time delay (55 min.). These changes persisted for similar length as those in the spectra of the HLA disparate individuals. This result implies that the allegenaic stimulation spectra of individuals who share some HLA alleles exhibit spectral changes suggestive of activation at longer time intervals. This implication is supported also through the use of tissue culture medium instead of saline for the incubation medium which in theory should enhance lymphocyte activation times.

The time series infrared spectra of the allegenaic stimulated lymphocytes from HLA identical siblings exhibit none of the changes suggestive of lymphocyte activation over the whole 180 min. time period supporting the hypothesis that the allegenaic stimulated infrared spectra of individuals with compatible immunologic alleles take a longer incubation time period to exhibit spectral changes suggestive of activation. In the case of the HLA identical twins we would not expect to observe such changes, however only a longer time series study will confirm this hypothesis. These preliminary results demonstrate the potential of IR spectroscopy to revolutionise matching protocols in the area of tissue transplantation. The chemical information available from the infrared spectra should also help clarify the biochemistry of activation.

The claims defining the invention are as follows:

1. A method for determining a cellular function or a change in cellular function, the method including:

contacting a sample of cells with an activating agent;

directing a beam of infrared light at the sample of cells;

analyzing the infrared spectrum of the sample at at least one range of frequencies; and ascertaining whether at least one change in the infrared spectrum has occurred due to the activation of the cells that can be correlated to the cellular function or a change in cellular function by the activating agent and determining the cellular function or the change in cellular function therefrom, wherein the sample is a body fluid containing said cells.

2. A method according to claim 1, wherein the sample is blood or a component thereof containing at least one cellular component selected from the group consisting of lymphocytes, erythrocytes and platelets.

3. A method according to claim 1, wherein the cells are immunocompetent cells sensitized to an antigen.

4. A method according to claim 3, wherein the immunocompetent cells are lymphocytes.

5. A method according to claim 1, wherein the infrared light is produced by a Fourier Transform Infrared spectrometer.

6. A method according to claim 1, wherein the infrared light is produced by a Raman confocal spectrometer.

7. A method according to claim 1, wherein the activating agent is one or more mitogens.

8. A method according to claim 1, wherein the activating agent is one or more antigens.

9. A method according to claim 1, wherein the activating agent is selected from the group consisting of a monoclonal antibody, polyclonal antibody and a ligand to a cell component.

10. A method according to claim 1, wherein the cellular function or change in cellular function determined is cellular immunocompetence.

11. A method according to claim 10, wherein the cellular function or change in cellular function determined is cellular immunocompetence and wherein the sample is taken from a subject with immunodeficiency, autoimmunity, potential contact with infection disease, allergies, hypersensitivy or cancer.

12. A method according to claim 1, wherein the cellular function or a change in cellular function determined is tissue compatibility for transplants.

13. A method according to claim 1, when the method is used to determine tissue compatibility for tissue or organ transplant.

14. A method according to claim 1, wherein the analysis of the infrared spectrum includes analysis of spectral characteristics of at least one range of frequencies to ascertain whether (a) at least one change in the infrared spectral characteristics has occurred due to vibration of at least one functional group of molecules, (b) at least one change in the infrared spectral characteristics has occurred due to conformational changes of at least one functional group of molecules, or both (a) and (b) in the sample.

15. A method according to claim 14, wherein the at least one change in the infrared spectra characteristic is a change in absorption intensity at a particular frequency or a change of frequency at which a particular absorption occurs.

16. A method according to have claim 14, wherein the at least one functional group is in at least one molecule selected from the group consisting of carbohydrates, nucleic acids, lipid molecules, proteins, glycoprotein, and glycogen.

17. A method according to claim 14, wherein the at least one functional group is selected from the group consisting of a phosphodiester group, a C—OH group, a CH group and $CH_3$.

18. A method according to a claim 1, wherein the analysis of the infrared spectrum of the sample is carried out two or more times.

19. A method according to claim 1, wherein the at least one range of frequencies is in the range of 950 cm$^{-1}$ to 1650 cm$^{-1}$.

* * * * *